(12) United States Patent
Seufert

(10) Patent No.: US 6,668,403 B2
(45) Date of Patent: Dec. 30, 2003

(54) IMAGING MEDICAL EXAMINATION APPARATUS HAVING A BEARING MECHANISM

(75) Inventor: Matthias Seufert, Oberreichenbach (DE)

(73) Assignee: Siemens Aktiengesellschaft, Münich (DE)

(*) Notice: Subject to any disclaimer, the term of this patent is extended or adjusted under 35 U.S.C. 154(b) by 111 days.

(21) Appl. No.: 10/080,803

(22) Filed: Feb. 22, 2002

(65) Prior Publication Data

US 2002/0112288 A1 Aug. 22, 2002

(30) Foreign Application Priority Data

Feb. 22, 2001 (DE) .......................... 101 08 635

(51) Int. Cl.⁷ .............................. A61G 7/10; A61G 7/00
(52) U.S. Cl. ........................... 5/601; 5/81.1 C; 378/209
(58) Field of Search ................. 5/601, 943, 81.1 R, 5/88.1, 81.1 C; 378/209, 208

(56) References Cited

U.S. PATENT DOCUMENTS

| 4,131,802 A | * 12/1978 | Braden et al. ............... 378/208 |
| 4,914,682 A | * 4/1990 | Blumenthal .................. 378/209 |
| 5,475,884 A | * 12/1995 | Kirmse et al. ................. 5/601 |
| 2002/0104163 A1 | * 8/2002 | Reimann ....................... 5/601 |

FOREIGN PATENT DOCUMENTS

| DE | 42 24 036 | * 5/1993 |
| DE | 197 49 783 | * 5/1999 |

* cited by examiner

Primary Examiner—Alexander Grosz
(74) Attorney, Agent, or Firm—Schiff Hardin & Waite

(57) ABSTRACT

A bearing mechanism or support structure for an imaging medical examination apparatus, particularly a magnetic resonance apparatus or a computer tomography apparatus, has a bearing plate for the patient and an endless conveyor band or belt for transporting the bearing plate through an opening in the examination apparatus. The conveyor band can move through the opening that serves for the acceptance of the patient and is moved therethrough by means of two end rollers arranged on mutually opposite sides of the examination apparatus.

10 Claims, 5 Drawing Sheets

IMAGING MEDICAL EXAMINATION APPARATUS HAVING A BEARING MECHANISM

BACKGROUND OF THE INVENTION

The present invention is directed to an imaging medical examination apparatus, particularly a magnetic resonance apparatus or a computer tomography apparatus, in which the examination apparatus comprises a through opening for the acceptance of an examination subject or of a patient to be examined. A bearing or support mechanism for the examination apparatus includes a bearing plate for the examination subject or patient.

In magnetic resonance apparatus, particularly nuclear magnetic resonance tomographs, as well as computer tomography apparatus, it is standard to scan a patient in a longitudinal direction to obtain a three-dimensional scanning of the patient. In computer tomography, the patient is introduced into an opening of a gantry for this purpose and is conducted therethrough in steps or continuously until the region of the patient to be examined has been completely scanned. An acceptance region or examination region is, thus, located in the opening, wherein a two-dimensional disk-like image is registered at each step. In nuclear magnetic resonance tomography, the patient is introduced into an opening of a housing that, for example, encompasses a magnet. The patient must be moved to such an extent until the body part to be examined is positioned in the exposure region. A 3D data set can be generated after the patient has arrived at this position.

U.S. Pat. No. 5,475,884, whose disclosure is incorporated herein by reference thereto and which claims priority from German Application 42 24 036, discloses a patient supporting apparatus or bearing apparatus to introduce a patient in an opening of a medical apparatus, such as a computer tomograph.

It is required for some examinations to implement a scan that covers the entire body of the patient. This should occur without repositioning the patient in order to avoid any unnecessary stress on the patient and also on the personnel operating the examination device. The known bearing mechanism comprises a bearing plate for the examination subject or patient that can be introduced into the opening boom-like proceeding from one side of the opening. The known bearing mechanism is limited in terms of its scan length, so that numerous examinations cannot be implemented with it

SUMMARY OF THE INVENTION

The present invention is based on the object of providing an examination apparatus so that greater scan lengths can be achieved.

This object is inventively achieved by an examination apparatus that comprises an endless and/or circulating conveyor belt or endless and/or circulating conveyor band for transporting the bearing plate into and through an examination apparatus. The arrangement includes at least two end rollers or deflection rollers on opposite sides of the examination apparatus for moving a conveyor band or a conveyor belt in two opposite directions between the end rollers, so that the conveyor band or, respectively, conveyor belt can be moved through the opening at least in one direction.

The bearing or support mechanism of the examination apparatus accordingly comprises a circulating continuous band or circulating continuous cable, which has the advantage that the bearing plate can be displaced over a great distance and, thus, a large scan region can be realized. What is understood by a deflection roller in conjunction with the invention is every rotatable or stationary element with which the change in direction of the belt can be achieved, such as the end of a belt, and can be, for example, a wheel or a shaft. The conveyor belt could, for example, also be referred to as a conveyor string, conveyor cable or conveyor wire.

An opening in the sense of the invention need not necessarily be enclosed on all sides. For example, it can be established by the interior of a C-shaped component part by a recess or by a cavity.

According to a preferred embodiment, the conveying length of the conveyor band and/or belt is greater than twice the height of an adult human patient and greater than four meters. What is thereby referred to as a conveying length is a length over which an article can be transported with the assistance of the conveyor band and/or conveyor belt. When the conveyor band or belt is respectively deflected oppositely in parallel by the deflection or end roller, the total length of the conveyor band or conveyor belt is approximately at least twice as great as the entire conveying path. Given the implementation of the conveyor band or belt with the preferred length, an advantage occurs for the bearing mechanism that a patient can be comfortably placed on one side of the medical examination apparatus and the entire length of the patient can be conducted through the opening and, thus, can be scanned.

Preferably, the conveyor band or belt is implemented elastically at least on its surface and, in particular, has an inside equipped with extension-reducing fibers.

According to another preferred embodiment, the bearing plate and/or conveyor band or belt is fashioned so that the bearing plate can be transported by the conveyor band or belt on the basis of a non-positive lock, particularly on the basis of frictional force. As a result thereof, it is possible in an especially simple way to bed the patient onto the bearing plate when the bearing plate is removed and to couple the bearing plate together with the patient to the conveyor band or belt. The coupling, for example, occurs only in that the bearing plate is placed on the conveyor band or belt. The frictional forces generated by the weight of the bearing plate between the bearing plate and the conveyor band or belt suffices, in particular, for moving the bearing plate forward.

For example, the bearing plate and the conveyor band or belt, thus, engage non-positively as well as positively in one another. The conveyor belt or band can comprise a toothing for this purpose, whose teeth engage into recesses on an underside of the bearing plate.

Preferably, the bearing plate and the conveyor band or belt do not engage positively into one another, particularly that the bearing plate is freely displaceable in the conveying direction on the conveyor band or belt. The advantage for the operating personnel occurs therefrom that the bearing plate can be placed onto the conveyor band or belt without having to pay attention to an engagement of the positive locking elements.

There is preferably no fixed connection between the bearing plate and the conveyor band or belt. In the case of the positive implementation with toothing and recesses, this means that the bearing plate can be separated from the conveyor belt or band merely by lifting and removing the teeth from the recesses.

The bearing plate, thus, largely lies loosely on the conveyor band or belt. Guide rails or retaining rails can be present for lateral guidance.

The conveyor band or belt is preferably fabricated of a plastic material, particularly rubber, and is optimally fabricated of soft component parts. The implementation of the conveyor band or belt with a plastic material has the advantage that no metal parts for disturbing the operation of either a nuclear magnetic resonance tomograph or of a computer tomograph are introduced into the examination region. This, for example, cannot be avoided if a worm drive having a metallic worm were present instead of the conveyor belt, and the metallic worm extends through the opening of the medical examination apparatus.

In order to avoid disturbing metallic influences, the bearing plate is also fabricated to be metal-free to the farthest reaching extent and is essentially composed of a plastic reinforced with fiberglass or reinforced with aramid fibers for magnetic resonance examinations and is essentially composed of plastic reinforced with carbon fibers or aramid fibers for computer tomography purposes.

The conveyor belt is preferably conducted horizontally with a flat side, so that the bearing plate can be placed onto the conveyor band with its underside engaging the band. In particular, at least one of the deflection rollers is driven by a drive means for driving the conveyor band or, respectively, conveyor belt.

Alternatively or additionally, a drive motor can be integrated into a foot or base of the bearing mechanism. A drive roller for driving the conveyor band or belt can also be integrated into the foot.

Other advantages and features of the invention will be readily apparent from the following description of the preferred embodiments, the drawings and claims.

DESCRIPTION OF THE PREFERRED EMBODIMENTS

Figure 1:
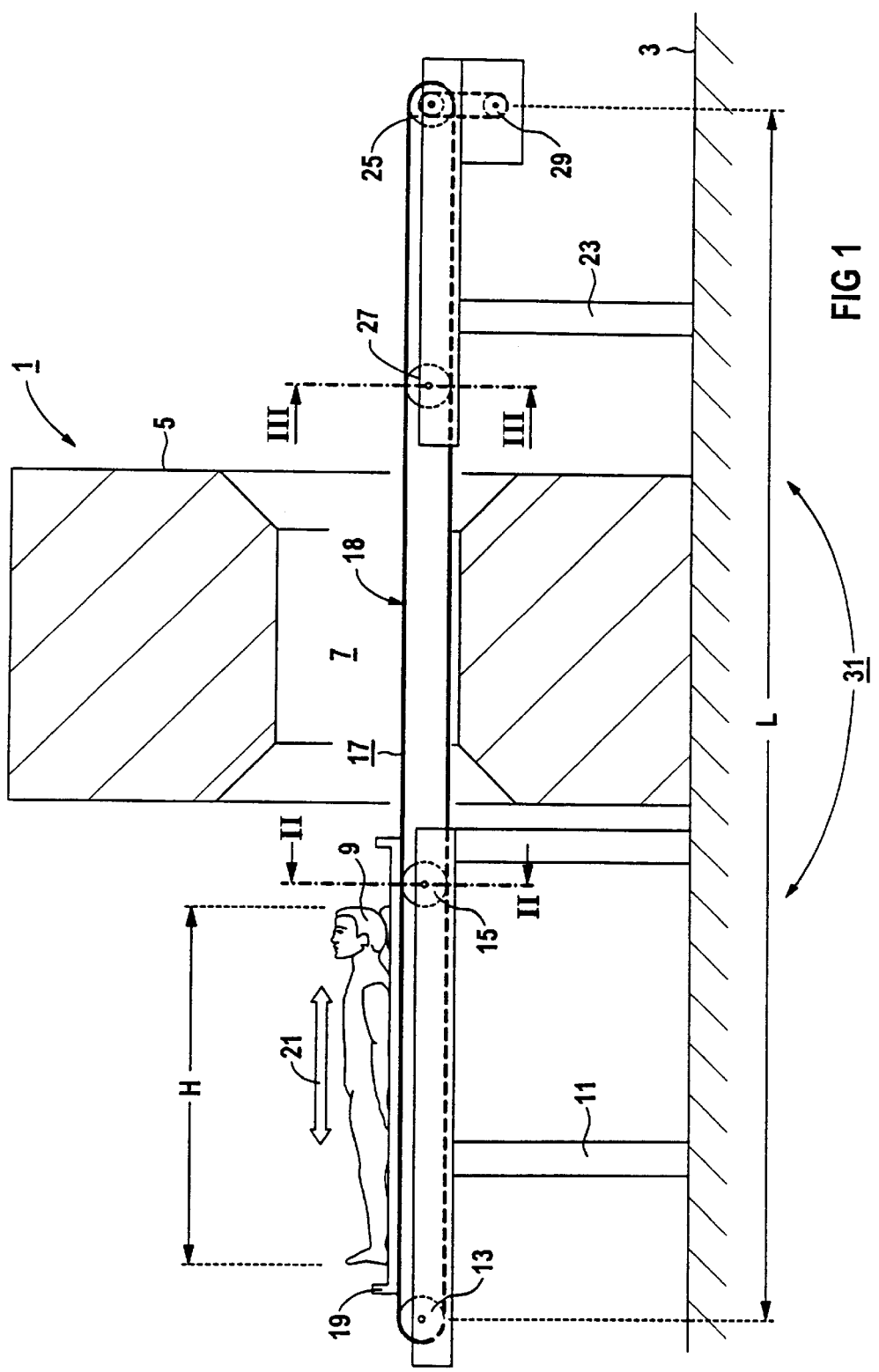
FIG. 1 is a longitudinal cross section with portions in elevation of an examination apparatus utilizing the first exemplary embodiment of a support mechanism according to the present invention.

The principles of the present invention are particularly useful for a support structure or bearing mechanism, generally indicated at 31 in FIG. 1, for an imaging medical examination apparatus, generally indicated at 1. The medical examination apparatus 1 may be a nuclear magnetic resonance tomography apparatus. The examination apparatus comprises a housing 5 which stands on the floor 3 and is shown in cross section. A magnet (not shown in greater detail) is arranged in the housing 5. The housing 5 has an opening 7 through which a patient, who is to be scanned, is introduced into the device for scanning in an imaging fashioned in a specific exposure or examination region.

The bearing mechanism or support structure 31 is disposed on the floor 3 and includes a supporting unit 11 which, as illustrated, supports an end or deflection roller 13 and an idler roller or supporting roller 15. In addition, a second supporting unit 23 is disposed on the opposite side of the housing 5 from the first-mentioned unit 11 and also includes an end roller 25 and a support roller 27. An endless band or belt 17 is received on these rollers and provides a flat upper surface 18 which receives a bearing plate 19 on which a patient 9 is positioned. The bearing plate or bedding board 19 is not firmly connected to the conveyor belt 17 and can be removed therefrom by being simply lifted up.

With the conveyor belt 17, the bearing plate 19 together with the patient 9 can be introduced into the opening 7 along the direction indicated by the double-arrow 21 and can be conducted through this opening 7 and be moved back in turn in the reverse direction. To this end, the support 23 which has the second end roller 25 and a further supporting roller 27 is present on the opposite side of the examination apparatus 1. The conveyor belt 17 rotates endlessly between the two end rollers 13 and 25 with the upper part running in the one direction while the lower part of the belt 17 is running in the opposite direction through the opening 7. Since the conveyor length L of the conveyor belt 17 is greater than twice the height H of the patient 9, it is possible to move the patient 9 completely through the opening 7 once the patient has been placed on the bearing plate 19.

For driving the conveyor belt 17, a drive means 29, for example an electric motor, is attached to the support 23, and this drive means 29 drives the second end roller 25. The conveyor belt is fabricated of elastic rubber reinforced with fiberglass skeins and is conducted with low mechanical tension around the end rollers 13 and 25. For maintaining the mechanical pre-stress given extension of the conveyor belt 17 fabricated of rubber that will occur over time despite the reinforcing skeins, one of the end rollers 13 or 25 or one of the supporting rollers can be adjusted out of the illustrated position, so that a lengthening of the running distance of the conveyor belt 17 can occur.

As a result thereof, the conveyor belt 17 is fabricated of a high-friction material, such as rubber, and suffices for moving the bearing plate 19 that is later placed onto the conveyor belt 17. A positive engagement is not required. As a result of the frictional engagement, the placing of the bearing plate 19 on the conveyor belt 17 is easily facilitated. The entrainment of the bearing plate by the conveyor belt 17 occurs only as a result of the force of friction. For supporting this effect, the underside of the bearing plate 19 can be roughened or can be provided with a friction-increasing means in some other way.

The supporting unit 11, the conveyor belt 17, the support unit 23 and the bearing plate 19 form a bearing or support structure 31.

Figure 2:
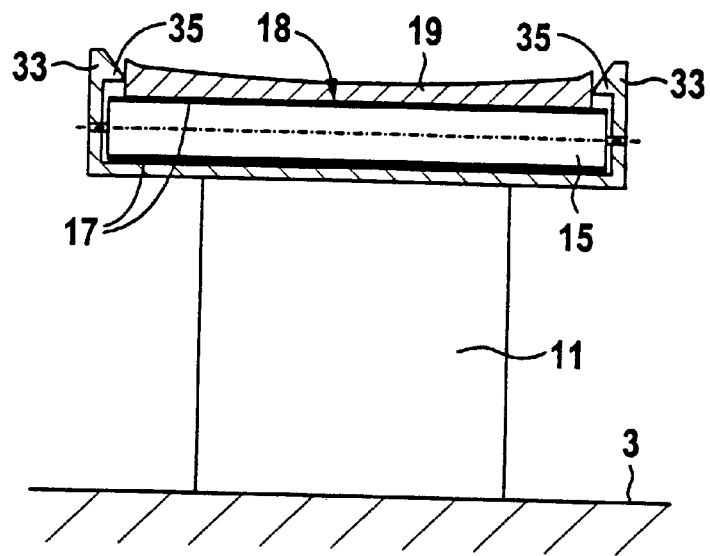
FIG. 2 is a cross sectional view taken along the lines II—II of FIG. 1.

As already mentioned, the bearing plate 19 lies loosely on the conveyor belt 17 to the farthest-reaching extent. For lateral guidance, guide rails 33 (FIG. 2) are attached to the supporting unit 11 along the conveyor belt 17. These guide rails use guide jaws 35 to act on the lateral surfaces of the bearing plate 19. The guide rails 33 do not surround the bearing plate, so that a simple removal of the bearing plate in an upward direction is possible.

Figure 3:
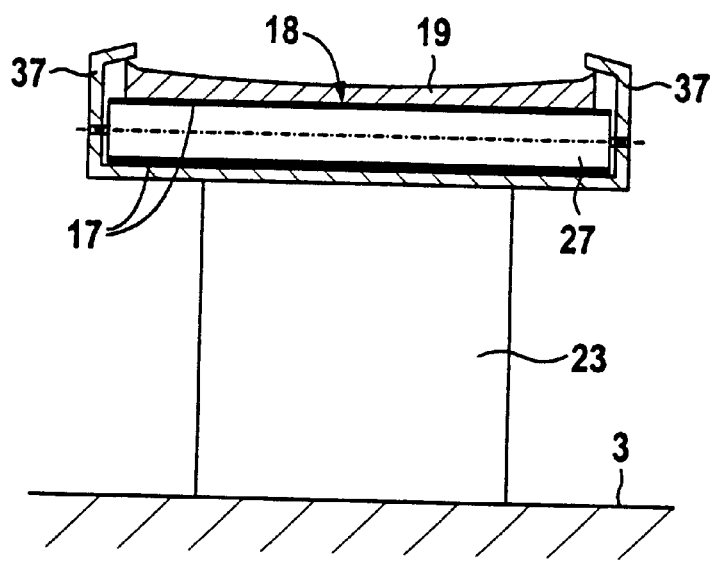
FIG. 3 is a cross sectional view taken along the lines III—III of FIG. 2.

FIG. 3 shows a cross section of the bearing plate 19 that has already passed through the opening 17 to the opposite side. For lateral guidance and holding of the bearing plate 19, the support 23 has retaining rails 37 that embrace the bearing plate 19 along a top edge, so that a tilting of the bearing plate 19 around a horizontal axis is suppressed. Such a tilting would derive if the length of the support 23 were substantially shorter than the length of the bearing plate 19.

In order to avoid such a tilting, the guide rails 33 of the supporting unit 11 can also be implemented like the retaining rails 32 of FIG. 3 in a sub-region that is adjacent the housing 5 of the examination apparatus 1.

The supporting units, such as 11 and 23, are, in particular, constructed as height adjustable and independently of one another as well.

Figure 4:
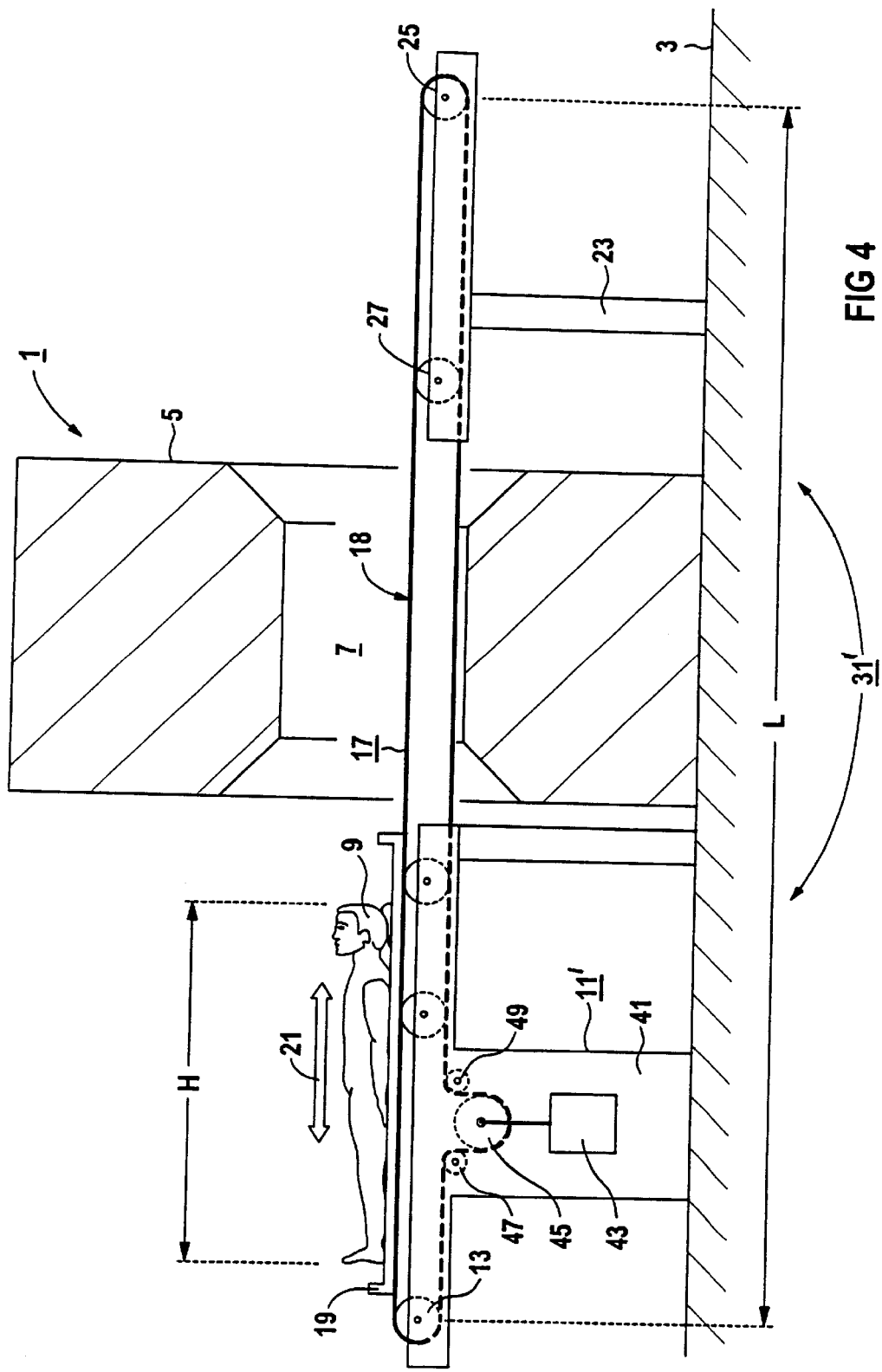
FIG. 4 is a longitudinal cross sectional view with portions in elevation of an examination apparatus utilizing a second exemplary embodiment of the support mechanism of the present invention.

In FIG. 4, the embodiment of the bearing mechanism or support structure 31' is illustrated and is largely identical to the embodiment 31 of FIG. 1. In contrast to the embodiment of FIG. 1, a drive motor 43 is integrated in a foot or base 41 of the supporting unit 11', as shown in FIG. 4. A drive roller 45 is also provided in the foot 41 and the conveyor belt 17 is then conducted around this drive roller 45 with the assistance of deflection rollers, such as 47 and 49. The drive roller 45 is driven by the drive motor 43. Also, it should be noted that an additional supporting roller, in addition to the rollers 15, is illustrated.

Figure 5:
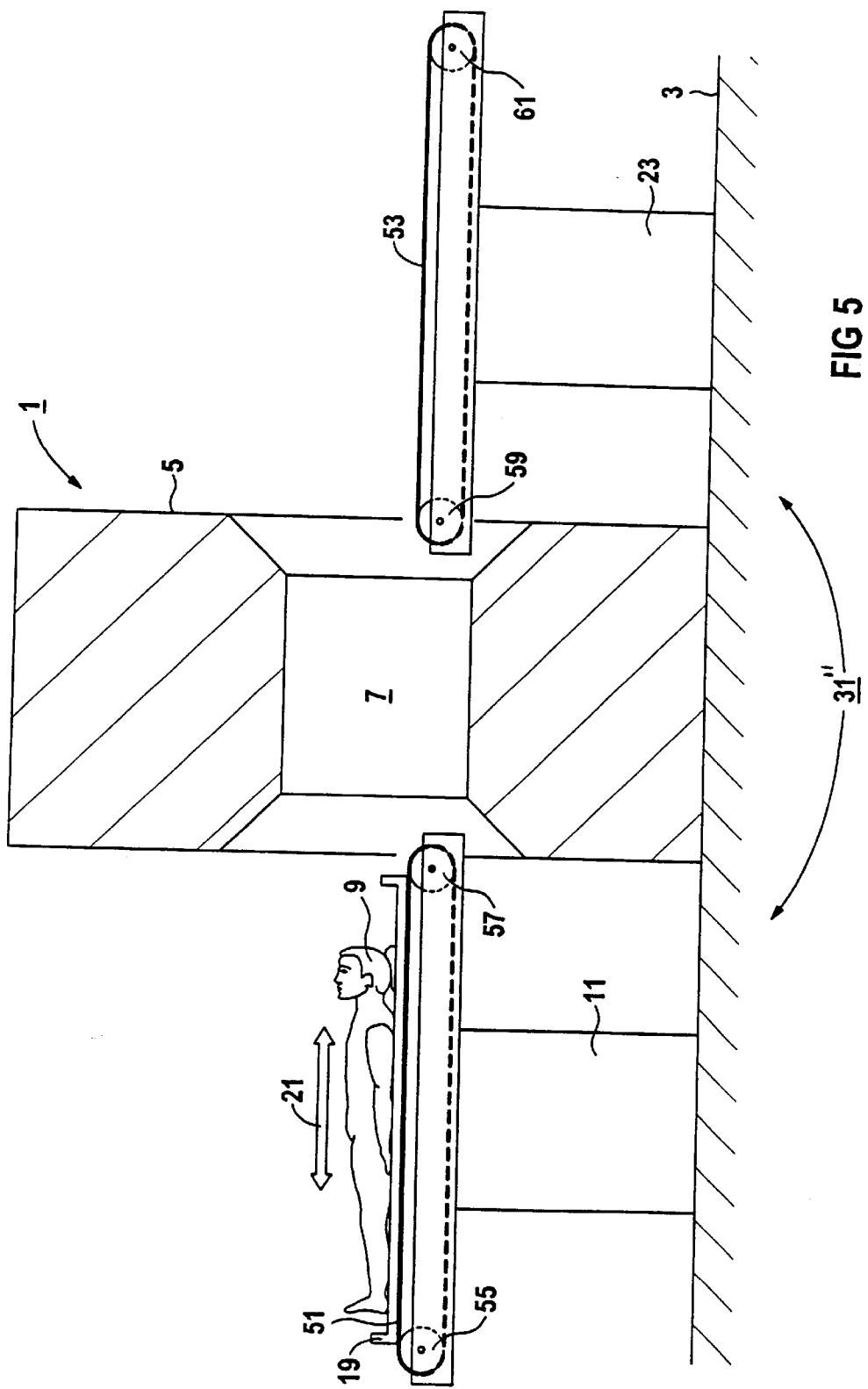
FIG. 5 is a longitudinal cross sectional view with portions in elevation of an examination apparatus utilizing a third exemplary embodiment of the support mechanism according to the present invention.

As already explained, one aspect of the invention is the employment of a conveyor belt 17, which is conducted through the opening 7. Another aspect of the invention is described hereinbelow, and is capable of being realized independently of this conveyor belt aspect. In this arrangement, the coupling of the bearing plate 19 to the conveyor belt by a non-positive lock, particularly due to the force of friction, whereby a positive lock is advantageously foregone. Such a coupling is also utilized given a bearing mechanism that comprises two separate conveyor belts 51 and 53, as illustrated in FIG. 5, in place of the single conveyor belt which extends through the opening 7, as illustrated in the embodiment of FIGS. 1 and 4. The two conveyor belts 51 and 53 extend into the opening from mutually opposite sides of the examination apparatus 1. Particularly in view of this material selection, such conveyor belts 51 and 53 can be fashioned like the conveyor belt of the initially-cited, preferred development of the claimed bearing mechanism or like the conveyor belt 17 of FIGS. 1 through 4. Corresponding developments and embodiments, likewise, can be provided.

As shown in FIG. 5, the bearing mechanism 31" has two separate conveyor belts 51 and 53. The conveyor belts 51 comprises two end rollers 55 and 57 which are mounted in the support 11 and the belt 53 has two end rollers 59 and 61 in the support 23. The supporting unit 11 of the conveyor belt 51 on the left side is height-adjustable independently of the height-adjustable support 23 of the conveyor belt 53 on the right side. The conveyor belts 51 and 53 immediately preceding the housing at the housing side, so that a gap, which has a width approximately corresponding to the depth of the housing 5, is formed therebetween. The conveyor belts 51 and 53 are driven so that they convey with identical speed and always in the same direction.

It is noted that each of the units supporting the belts 51 and 53 adjacent the end rollers, such as 57 and 59, respectively, will require retaining rails, such as 37 of FIG. 3, to prevent tilting of the bearing plate 19 as it is being transferred off and onto each of the conveyor belts 51 and 53.

Figure 6:
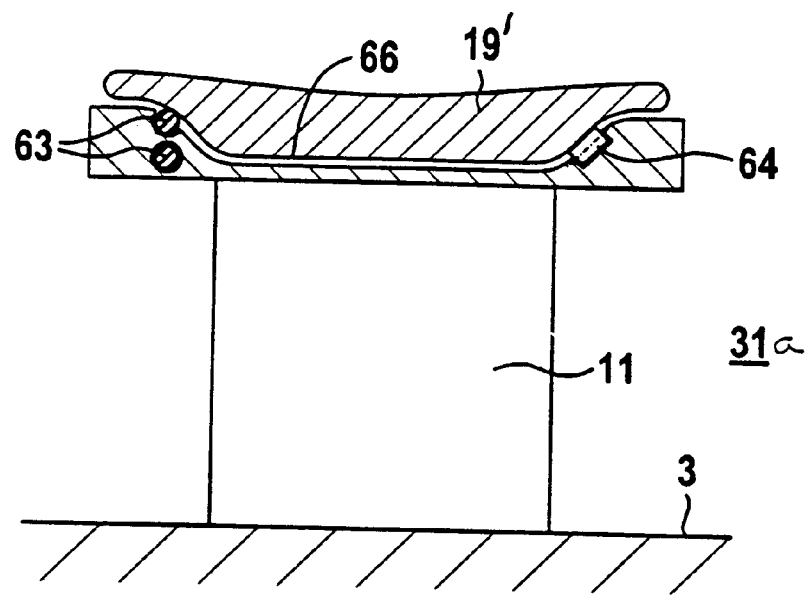
FIG. 6 is a cross sectional view similar to FIG. 2 showing a fourth exemplary embodiment of a bearing support mechanism of the present invention.

An exemplary embodiment 31a, which is largely identical to the exemplary embodiment 31 of FIG. 1, is shown in FIG. 6. This embodiment has a conveyor belt 63 having a circular cross section which is present instead of a flat conveyor band 17. The conveyor belt 63 is conducted in the supporting unit 11 so that at least one side projects out of the housing of the support unit 11 and can be, thus, enter into contact with an underside of a bearing plate 19'. The conveyor belt 63 is returned under this position so that the conveyor belt 63 circulates endlessly. Supporting rollers that are not explicitly shown can be present for supporting, in particular, the respective upper parts of the conveyor belt 63. Glide means, such as rollers or guide rollers 64, are present at the opposite side of the bearing plate 19', and these are also in contact with the bearing plate 19'.

As illustrated, the bearing plate 19', on an underside, comprises an applied portion 66 whose width is dimensioned so that the bearing plate 19' is guided between the conveyor belt 63 at the one side and the guide rollers 64 at the opposite side. As a result thereof, the guide rails 33 with the guide jaws 35 can be omitted in an especially advantageous way compared to the embodiment of FIG. 2. An especially space-saving and ergonomically favorable structure of the bearing mechanism 31a is possible in this way.

Figure 7:
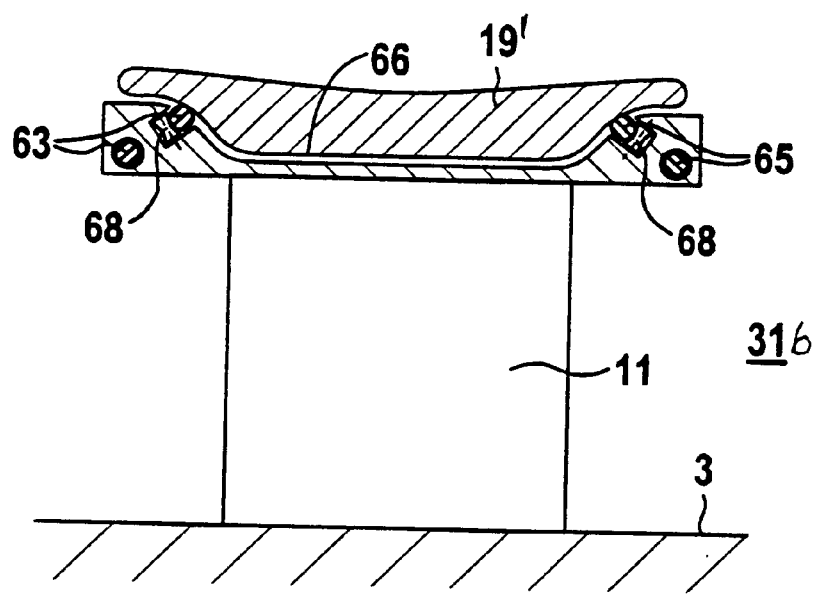
FIG. 7 is a cross sectional view similar to FIG. 2 of a fifth exemplary embodiment of a bearing mechanism or support structure according to the present invention.

FIG. 7 shows a fifth embodiment of the bearing mechanism 31b, wherein, in contrast to the exemplary embodiment of FIG. 6, two conveyor belts 63 and 65 are present. These two belts engage opposite sides of the applied portion 66 of the bearing plate 19'. The two guide belts 63 and 65 are supported by supporting rollers 68. The two guide belts 63 and 65 are driven synchronously running in the same direction. To this end, in particular, they are driven by one and the same driver roller (not shown). The respectively returning part of the conveyor belt 63 or 65, respectively, runs back laterally or slightly obliquely under the advancing part. This arrangement makes it possible for a low structural height.

Although various minor modifications may be suggested by those versed in the art, it should be understood that I wish to embody within the scope of the patent granted hereon all such modifications as reasonably and properly come within the scope of my contribution to the art.

I claim:

1. An imaging medical examination apparatus having an opening for the acceptance of the examination subject, a support structure for introducing the examination subject into the opening, said support structure comprising a bearing plate for receiving the examination subject, end rollers disposed on opposite sides of the examination apparatus, an endless conveyor band extending through the opening and received on the end rollers, said bearing plate engaging said endless conveyor band and means for moving the band to move the bearing plate back and forth through the opening of the examination apparatus.

2. An imaging medical examination apparatus according to claim 1, wherein the length of the conveyor band between the two end rollers is greater than twice the height of an adult patient and greater than four meters.

3. An imaging medical examination apparatus according to claim 1, wherein the conveyor band is elastic, at least on its surface, and comprises extension-reducing fibers.

4. An imaging medical examination apparatus according to claim 1, wherein the bearing plate is constructed so that it engages the conveyor band for transport by the conveyor band by means of a non-positive lock and relies on the force of friction.

5. An imaging medical examination apparatus according to claim 4, wherein the bearing plate and conveyor band do not engage into one another with a positive lock.

6. An imaging medical examination apparatus according to claim 1, wherein the conveyor band is fabricated of plastic and is optimally fabricated of further component parts.

7. An imaging medical examination apparatus according to claim 1, wherein the conveyor band is horizontally guided with one flat side so that the bearing plate can have its underside placed onto the conveyor band.

8. An imaging medical examination apparatus according to claim 1, wherein the means for moving the band includes driving at least one of the end rollers by a drive means.

9. An imaging medical examination apparatus according to claim 1, wherein a foot on one side of the examination device contains a drive motor of the means for moving.

10. An imaging medical examination apparatus according to claim 9, wherein the drive motor engages a drive roller which is integrated into the foot.

* * * * *